United States Patent
Schmitz

[11] Patent Number: 5,807,353
[45] Date of Patent: Sep. 15, 1998

[54] ASPIRATION DEVICE WITH SEPARATING ELEMENT

[76] Inventor: Thomas David Schmitz, 2643 Carisbrook Dr., Oakland, Calif. 94611

[21] Appl. No.: 714,406

[22] Filed: Sep. 16, 1996

[51] Int. Cl.$^6$ .................................................. A61M 5/00
[52] U.S. Cl. ..................... 604/264; 604/173; 604/319; 604/315; 604/313; 604/190; 604/4
[58] Field of Search ................................ 604/48, 902, 4, 604/27, 35, 190, 313, 315, 319, 320, 321, 264, 173

[56] References Cited

U.S. PATENT DOCUMENTS

| | | | |
|---|---|---|---|
| 4,083,706 | 4/1978 | Wiley | 55/385 |
| 4,443,220 | 4/1984 | Hauer et al. | 604/408 |
| 4,468,217 | 8/1984 | Kuzmick et al. | 604/48 |
| 4,775,482 | 10/1988 | Thurman | 210/668 |
| 4,886,492 | 12/1989 | Brooke | 604/49 |
| 4,957,637 | 9/1990 | Cornell | 210/782 |
| 5,411,472 | 5/1995 | Steg, Jr. et al. | 604/4 |
| 5,531,672 | 7/1996 | Lynn | 604/4 |
| 5,569,209 | 10/1996 | Roitman | 604/190 |
| 5,630,939 | 5/1997 | Bulard et al. | 210/461.1 |

*Primary Examiner*—Michael Buiz
*Assistant Examiner*—Tina T. D. Pham
*Attorney, Agent, or Firm*—Samuel A. Kassatly

[57] ABSTRACT

An aspiration device for separating liquid content of a body fluid and irrigation fluid if any, from solid matters, includes an integrally formed housing, and an integrally formed separating element which is detachably inter-connectable to the housing. The housing includes a proximal segment for defining a hollow space to receive part of the separating element. The separating element includes a filter element for separating the liquid content of the body fluid from the solid matters and for collecting the solid matters in the interior of the filter element. The separating element further includes an end connector for interlocking the separating element with the housing, and an egress tube for conveying the separated liquid content outside the aspiration device. The filter element includes a filter that fits within the housing proximal segment, so that when the separating element is locked in an operating position with the housing, the filter is held coaxially within, and at a distance from the housing, to form an inner chamber between the separating element and the housing proximal segment, such that the liquid content of the body fluid passes through the inner chamber prior to exiting the aspiration device.

20 Claims, 2 Drawing Sheets

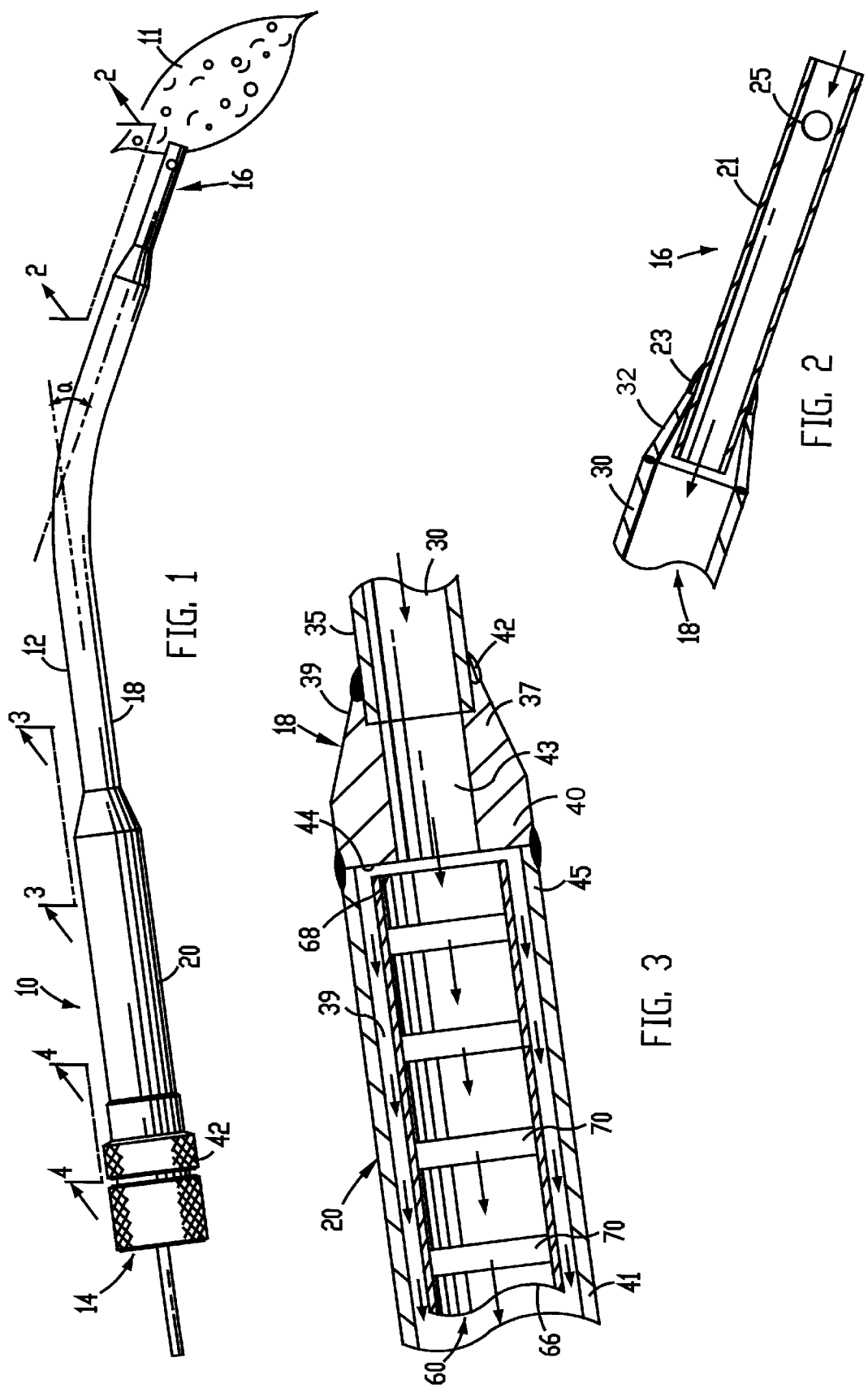

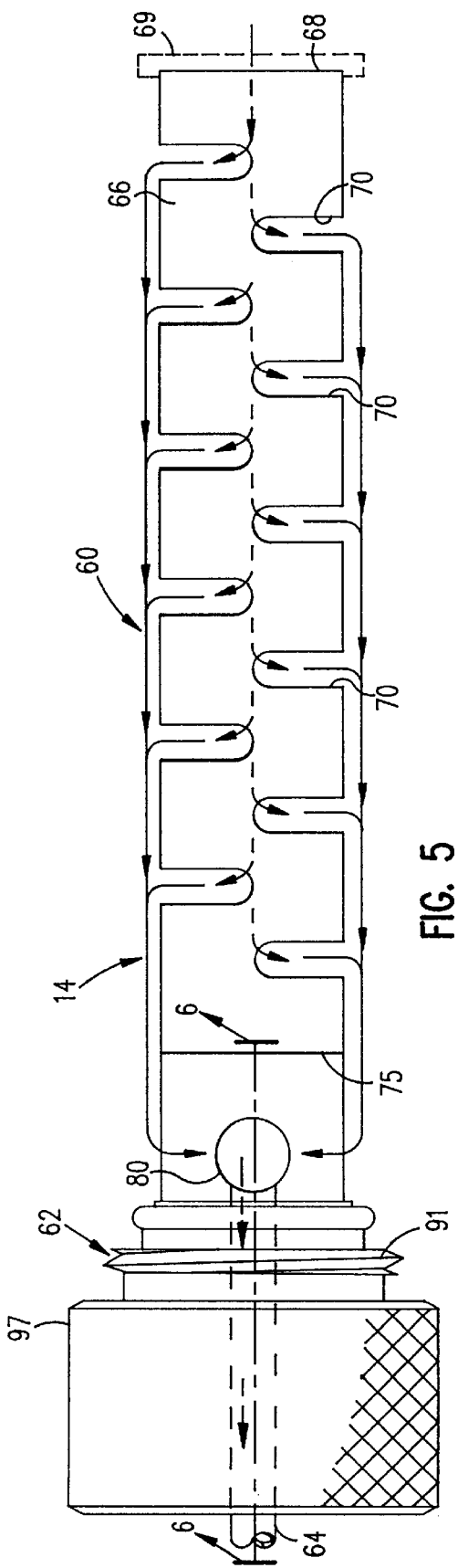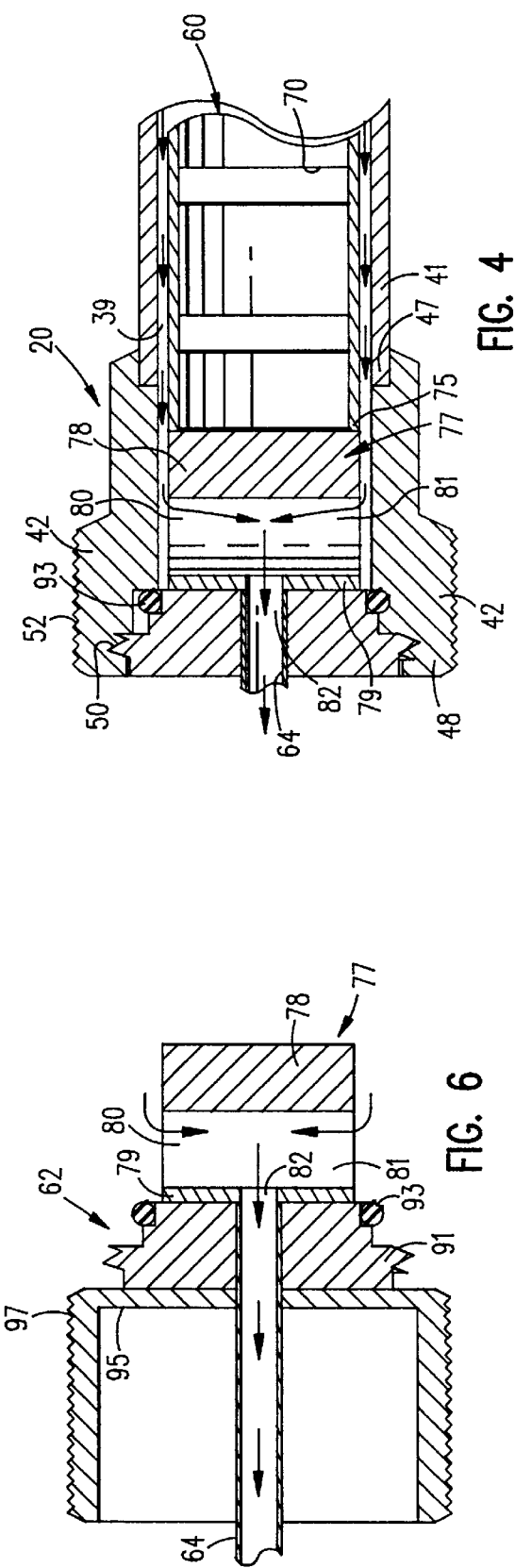

ASPIRATION DEVICE WITH SEPARATING ELEMENT

BACKGROUND OF THE INVENTION

1. Field of the Invention

The present invention relates in general to surgical equipment, and it more particularly relates to a new multi-purpose aspiration device, such as a suction tip, having a separating element. The aspiration device may be used to separate the liquid content of body fluid such as blood and serum from solid matters such as unwanted debris (e.g., bone fragments, tissue or like matter) in orthopedic and suction lipectomy surgeries. The aspiration device of the present invention may also be used as a collagen gathering device, an instrument for transferring specimen, a blood recovery system, as well as in other surgical and medical applications.

2. Background Art

Suction tips with filters have been well known and commonly used in surgeries for separating blood from waste material. For instance, U.S. Pat. No. 4,468,217 to Kuzmick et al., describes a surgical suction tip formed of an outer housing and an inner removable filter device. The housing includes a suction opening at one end and a filter receiving handle formed as a sleeve at the other end. The inner removable filter device is connected in the filter receiving handle by a quick connect-disconnect means, while the housing tapers so as to increase in size from its suction opening to the filter device. A seal is located between the housing and filter device.

However, the filter device has a relatively complex construction as it includes guide means for centering the filter device within the housing. The guide means includes equally spaced guide flanges extending radially outwardly from the filter device towards the inner surface of the filter receiving handle sleeve adjacent a short hollow conical section, such that the guide flanges guide the end of the filter device and position it within the filter receiving handle sleeve means.

In addition, the waste material flows in an annular space between the filter and the housing. The filter has openings to allow fluids to pass from the annular space inwardly to the inside of the filter. For this purpose, the free open end of the filter includes a cap member that closes the end of the filter in order to permit flow from the suction tube section into the annular space to the interior of the filter, through the filter openings. As a result, the solid waste matter collects within the annular space rather than in the interior of the filter, thus eventually clogging the annular space and the filter openings, and rendering the entire suction tip ineffective and difficult to clean and reuse.

U.S. Pat. No. 4,886,492 to Brooke addresses some of the foregoing concerns raised by the suction tip described in U.S. Pat. No. 4,468,217. The Brooke patent describes a surgical suction tip that includes a tubular body portion with a hollow tip portion at one end, and a cap portion releasably closing the other end. A tubular connecting portion is mounted externally on the cap portion and communicates therethrough into the body portion. A hollow filter member within the body portion defines an annular chamber between the filter member and the body portion and communicates with the tubular connecting portion through the cap portion. A plurality of apertures in the filter member connect the interior of the filter member with the annular chamber.

The body portion has location means that are integrally formed within the body portion adjacent the tip portion, to receive thereon and to locate one end of the filter member within the body portion, such that material entering the body portion through the tip portion flows into the hollow interior of the filter member. The other end of the filter member is closed. The filter member further includes a removable end cap located in, to close, the other end of the filter member. The end cap has a tapering annular skirt portion which is gripped between the other end of the body portion and the cap portion to locate the end cap within the body portion. The skirt portion of the end cap defines a plurality of apertures which interconnect the annular chamber with the tubular connecting portion by way of an aperture in the cap portion. It will be appreciated that the design of the end cap, including the skirt portion, and the location means forming part of the body portion, add to the manufacture complexity and use of the suction tip.

Wherefore, there is a great and still unsatisfied need for an aspiration device, such as a suction tip, which addresses and resolves the foregoing concerns. In addition, the new aspiration device should be useable in other medical and surgical applications, including but not limited to blood recovery systems.

A low blood trauma recovery system is described in U.S. Pat. No. 5,411,472 to Steg, Jr. et al., and is comprised of a suction wand in which liquid blood is separated from a mixture of blood and foam at the wound site through the transport of the two separated fluids at different velocities and negative gauge pressures. The wand includes an outer blood foam tube within which are three resiliently compressed, side-by-side tubes for handling liquid blood, rinse solution and anticoagulant. Low fluidic capacitance filter defoamer modules, having built-in diaphragm operated pumps, receive and filter recovered liquid blood and foam blood for transfer to separate storage bags.

SUMMARY OF THE INVENTION

It is therefore an object of the present invention to provide a new multi-purpose aspiration device, such as a suction tip. The aspiration device may be used to separate the liquid content of body fluid such as blood and serum from unwanted solid matters including debris, such as bone fragments, tissue or like matter in orthopedic and suction lipectomy surgeries. The new aspiration device may also be used as a collagen gathering device, an instrument for transferring specimen, a blood recovery system, as well as in other surgical, medical and non-medical applications. For instance, the aspiration device may be used in various laboratories.

The aspiration device is comprised of an integrally formed housing and an integrally formed separating element which is detachably inter-connectable to the housing. The housing includes a proximal segment for defining a hollow space to receive part of the separating element. The separating element includes a filter element for separating the liquid content of the body fluid from the solid matters and for collecting the solid matters in the interior of the filter element. The separating element further includes an end connector for interlocking the separating element with the housing, and an egress tube for conveying the separated liquid content outside the aspiration device. The filter element includes a filter that fits within the housing proximal segment, such that when the separating element is locked in an operating position with the housing, the filter is held coaxially within, and at a distance from the housing, to form an inner chamber between the separating element and the housing proximal segment, so that the liquid content of the body fluid passes through the inner chamber prior to exiting the aspiration device.

BRIEF DESCRIPTION OF THE DRAWING

The above and other features of the present invention and the manner of attaining them, will become apparent, and the invention itself will be best understood, by reference to the following description and the accompanying drawing, wherein:

FIG. 1 is a side view of an aspiration device according to the present invention, with its tip shown in proximity to an incision site;

FIG. 2 is a cross sectional view of the distal segment of the aspiration device of FIG. 1 taken along line 2—2;

FIG. 3 is a cross sectional view of the intermediate and proximal segments of the aspiration device of FIG. 1 taken along line 3—3;

FIG. 4 is a cross sectional view of an end connector forming part of the proximal end of the aspiration device of FIG. 1 taken along line 4—4;

FIG. 5 is a side elevational view of a separating element forming part of the aspiration device of FIG. 1, illustrating the fluidic flow of the body and other fluids containing solid, semi-solid or gelatinous debris; and FIG. 6 is a cross sectional view of a bypass threaded block, an end connector, and an egress tube of the separating element of FIG. 5 taken along line 6—6.

Similar numerals refer to similar elements in the drawing. It should be understood that the sizes of the different components in the figures are not necessarily in exact proportion or to scale, and are shown for visual clarity and for the purpose of explanation.

DETAILED DESCRIPTION OF THE PREFERRED EMBODIMENT

FIG. 1 illustrates a preferred embodiment of an aspiration device 10 according to the present invention, shown adjacent a body cavity or surgical incision 11. The aspiration device 10 is formed of a housing 12 and a separating element 14 that are detachably inter-connectable. In the present embodiment the separating element 14 is at least partially enclosed within the housing 12 and is threadably secured thereto. It should however be understood that other connecting means, such as a quick release connector may alternatively be employed.

During a surgical procedure the aspiration device 10 is used to remove blood, irrigating solution, and solid, semi-solid and gelatinous elements (herein collectively referred to as "solid matters" or "solid matter") such as bone fragments, fascia, and other debris from the incision 11, and possibly to collect the recovered blood for return to the patient. The aspiration device 10 separates the solid elements from the fluids by causing the solid elements to collect in the interior of the separating element 14. The aspiration device 10 may be easily and expeditiously cleaned by unthreading the housing 12 and the separating element 14; replacing or cleaning the separating element 14; and then securing the separating element 14 to the housing 12. The aspiration device 10 is also designed to improve the operating field visibility to the surgeon.

In the present illustration, the aspiration device 10 is fabricated from metal, preferably from stainless steel for optimal structural integrity, and to enable it to be sterilized and reused repeatedly. It should be clear that the aspiration device 10 may alternatively be disposable and formed of plastic, or any other suitable material.

The housing 12 is generally integrally formed of three main segments: a distal segment 16, an intermediate segment 18, and a proximal segment 20. The distal segment 16 will now be described in relation to FIGS. 1 through 3. The distal segment 16 includes a hollow, open-ended, cylindrical tip 21. One end of the tip 21 fits co-axially within the intermediate section, and is secured thereto by available methods such as by brazing or welding, as illustrated by the weld 23. The opposite end of the tip 21 includes one or more holes 25 that allow pressure relief when collecting fluid from the incision 11, in order to avoid damaging the adjacent tissue. In the present embodiment, the tip 21 includes three similar, radially oriented, and equidistally positioned holes 25. The hole diameter is approximately 50 mils ($50/1000$ inch). The tip 21 is approximately 1.5 inches in length, and has a diameter of approximately 0,25 inch and a thickness of approximately 50 mils. It should be clear to a person of ordinary skills in the art that while various dimensions are stated throughout the present specification for the purpose of illustration, it should be amply clear that other dimensions of the aspiration device 10, including the tip 21 may by selected. The tip 21 may be connected to an extension tube (not shown).

The intermediate segment 18 includes a hollow cylindrical tube 30, which, in a preferred embodiment, is uniform along its entire axial length, and has a circular cross-section. The tube 30 has a diameter of approximately 0.25 inch, a total axial length of approximately 2.5 inches, and a thickness of approximately 50 mils. The forward end of the tube 30 is rigidly secured to the tip 21 by means any available methods. For instance, in one example, the intermediate segment 18 includes a conically shaped, or tapered, hollow adapter 32 which is welded or brazed at one of its ends to the tube 30 and at its opposite end to the tip 21. The tube 30 is preferably bent at an angle "a" at about its middle so as to improve visibility to the surgeon.

In an alternative design the tube 30 may have a straight configuration. In yet another embodiment, the tube 30 may be eliminated altogether, with the tip 21 secured directly to the proximal segment 20. In still another embodiment, the tip 21 is threadably secured to the intermediate segment 18, thus enabling the surgeon to inter-change or replace the tip 21 easily and conveniently. According to a further embodiment, the intermediate segment 18 is formed of two or more tubular sections with progressively decreasing diameters so as to decrease the possibility of clogging and coagulation of the blood and other elements within the intermediate segment 18, prior to being separated by the separating element 14.

The proximal end 35 of the tube 30 is rigidly secured to the proximal segment 20 by available techniques. In a preferred embodiment, the intermediate segment 18 further includes a hollow connector 37 which is brazed or welded to the proximal end 35 of the tube 30 at its forward end 39, and to the proximal segment 20 at its rearward end 40.

The connector 37 is made of a solid block of metal with a central passageway 43 formed axially therein. One end of the central passageway 43 is adapted to snugly receive and to securely retain the proximal end 35 of the tube 30. The other end of the passageway 43 is cylindrically shaped and sized to match the shape and size of the inner surface of the tube 30, in order to ensure a smooth fluidic flow from the tube 30 to the proximal segment 20. The rearward end 40 defines an annular flat surface 44 facing the separating element 14. It should be understood that according to another embodiment, the tube 30 and the proximal segment 20 are detachable connected to each other, so as to optimize the interchangeability of either the tip 21 or the separating element 14.

The proximal segment 20 will now be described in detail with reference to FIGS. 1, 3 and 4. The proximal segment 20 defines a hollow space which is sufficiently large to receive part of the separating element 14, and to form an inner annular chamber 39 between the separating element 14 and the inner surface of the proximal segment 20. The proximal segment 20 includes two main components: a cylindrical tube 41, and an end connector 42 that are rigidly secured to each other, such that the entire housing 12 becomes a single integral piece.

The tube 41 is hollow and open ended. One end 45 of the tube 41 is secured to the rearward end 40 of the connector 37, and the opposite end 47 is rigidly secured to the end connector 42. The axial length of the tube 41 is approximately 3.75 inches, its inner diameter is approximately 0.875 mils, and the thickness of its wall is approximately 50 mils. The tube 41 is centered co-axially relative to the connector 37 and the tube 30. The end 47 of the tube 41 fits in part within the end connector 42.

The end connector 42 has a flared section 48, which, in conjunction with a corresponding section of the separating element 14 form a locking mechanism that allows the housing 12 to releaseably engage the separating element 14. In the present illustration, the flared section 48 includes internal threads 50. The outer surface 52 of the flared section 48 is optionally knurled for providing a convenient friction grip to the user while assembling or disassembling the aspiration device 10.

The separating element 14 will now be described in detail with reference to FIGS. 3 through 6. The separating element 14 generally includes a filter element 60 for separating the liquid fluid from the solid matters and for retaining the solid matters therewithin; an end connector 62 that interlocks the separating element 14 with the housing 12; and an egress tube 64 which conveys the separated liquid fluid to an external suction source (not shown).

The filter element 60 includes an open ended tubular filter 66 that fits within the tube 41 of the housing proximal segment 20. When the separating element 14 is locked in an operating position with the housing 12, filter 66 is held coaxially within, and at a distance from the inner surface of the housing tube 41, for defining the inner chamber 39 therewith. In the present example, the free distal end 68 is open and is maintained at a relatively short distance, for instance 5 mils, from the flat surface 44. In another embodiment, an annual compression bushing 69 (shown in dashed lines in FIG. 5) is secured to the distal end 68 and abuts the flat surface 44 of the connector 37 (FIG. 3), without interrupting the flow of the liquid fluid from the intermediate segment 18 to the filter element 60.

The filter 66 includes a plurality of peripheral openings 70. The openings 70 are arcuately formed, and extend about 135° for interconnecting the interior of the filter 66 with the inner chamber 39. According to the present embodiment, the openings 70 are similarly shaped and dimensioned, equidistally separated, and symmetrically interleaved so as to allow the separated liquid fluid to flow from the interior of the filter 66 to the inner chamber 39.

In this particular embodiment, the openings 70 are relatively large. For instance, the openings 70 may extend about 180° as is illustrated in FIG. 5, and the width of each opening 70 ranges between 0.125 inch and 0.3125 inch. According to another embodiment, the openings 70 are not identical. According to yet another embodiment, the openings 70 may be helically shaped. Other designs of the openings 70 are also contemplated. For instance the openings 70 may be circularly shaped and dispersed along the periphery of the filter 66. In another embodiment, the filter 66 is divided into two or more chambers with progressively larger openings such that each chamber is designed to separate and capture solid matters of different sizes.

The filter element 60 further includes a bypass block 77 having two opposite flat sides 78, 79. Side 78 is secured to the proximal end 75 of the filter 66 for completely closing it. The bypass block 77 is cylindrically shaped, and comprises two radial and diametrically opposed inlet ports 80, 81 that extend at 90° relative to the central axis of the separating element 14, throughout the width of the bypass block 77. The angular disposition of the inlet ports 80, 81 may vary in other embodiments.

The bypass block 77 also includes an axial outlet port 82 that extends centrally through the side 79, such that the liquid content of the fluid exiting the filter 66 passes within the bypass block 77 through the inlet and outlet ports 80, 81, 82. While two inlet ports 80, 81 and one outlet port 82 have been described, it should be understood that a portal having a different number of ports may be alternatively be formed within the bypass block 77, without departing from the scope of the present invention. According to a preferred embodiment, the diameter of the inlet and outlet ports 80, 81, 82 is approximately 0.25 inch.

The end connector 62 of the separating element 14 includes an externally threaded block 91 that interlocks the separating element 14 with the housing 12, and which, along with the flared section 48 forms the locking mechanism that allows the housing 12 to releaseably engage the separating element 14. The threaded block 91 includes a central bore that tightly receives the egress tube 64 in an axial co-linear relationship relative to the outlet port 82. The inner diameter of the egress tube 64 is similar to that of the port 82.

The threaded block 91 further includes a counterbore that provides a seat for an O-ring seal 93 which is compressed against a shoulder formed in the end connector 42 of the housing proximal segment 20. The O-ring 93 forms a fluid tight seal, and prevents the spillage of the separated liquid fluid outside the aspiration device 10.

The end connector 62 also includes a flat annular plate 95 and a hollow cylindrical knurled disconnect handle 97. The annular plate 95 is secured to the threaded block 91, and includes a central bore for allowing the egress tube 64 to pass therethrough. The handle 97 is optional, but facilitates the assembly and disassembly of the aspiration device 10.

The egress tube 64 is cylindrically shaped, and extends co-axially relative to the handle 97. The thickness of the egress tube 64 ranges between 25 and 509 mils. The free end of the egress tube 64 is connected to a suction source (not shown) for collecting the separated liquid fluid. Other dimensions may be used as needed for adequate egress.

To assemble the aspiration device 10, the surgeon holds housing 12 steadily with one hand, inserts the filter 66 inside the housing proximal segment 20 with the other hand, and then locks the housing 12 and the separating element 14 by rotating the end connector 64 into engagement with the housing end connector 42. In order to clean up the separating element 14 after use, or to disassemble the aspiration device 10, the surgeon simply twists the end connector 64 for disengaging it from the housing end connector 42. The separating element 14 containing the collected matter is then removed.

In use, the suction source exerts a suction effect on the tip 21 for drawing the body fluid into the tip 21 along paths defined by the arrows in the drawing. The body fluid is drawn from the tip 21 into the hollow interior of the housing intermediate segment 18, and therefrom to the interior of the filter 66 and then to the inner chamber 39 through the openings 70. The solid matters are captured by the filter 66, while the liquid content of the body fluid flows through the inlet and outlet ports 80, 81, 82 of the bypass block 77, and therefrom outside the aspiration device 10 via the egress tube 64.

While specific embodiments of the aspiration device and method of assembly and use have been illustrated and described in accordance with the present invention, modifications and changes will become apparent to those skilled in the art, without departing from the scope of the invention.

What is claimed is:

1. An aspiration device for separating liquid content of a body fluid and irrigation fluid if any, from solid matters, comprising in combination:
    an integrally formed housing;
    an integrally formed separating element detachably inter-connectable to said housing;
    said housing including a proximal segment for defining a hollow space to receive part of said separating element;
    said separating element including:
        a filter element for separating the liquid content of the body fluid and irrigation fluid from the solid matters, said filter element having a free, open, distal end for collecting the solid matters in the interior of said filter element;
        an end connector for interlocking said separating element with said housing; and
        an egress tube for conveying the separated liquid content outside the aspiration device;
    wherein said separating element being detachable from said housing in a single integral piece.

2. The aspiration device according to claim 1, wherein said filter element includes a filter that fits within said housing proximal segment, such that when said separating element is locked in an operating position with said housing, said filter is held coaxially within, and at a distance from said housing, to form an inner chamber between said separating element and said housing proximal segment.

3. The aspiration device according to claim 2, wherein said housing includes an intermediate segment which is integrally secured to said proximal segment; and
    wherein said free, open distal end of said filter is maintained at a short distance from said intermediate segment.

4. The aspiration device according to claim 3, wherein said short distance is approximately 5 mils.

5. The aspiration device according to claim 2, wherein said housing includes an intermediate segment which is integrally secured to said proximal segment; and
    wherein said free, open distal end of said filter is secured to an annular bushing for abutting against said intermediate segment, without interrupting the flow of the liquid content from said intermediate segment to said filter.

6. The aspiration device according to claim 2, wherein said filter includes a plurality of peripheral openings that interconnect the interior of said filter with said inner chamber.

7. The aspiration device according to claim 6, wherein said openings are arcuately formed, and extend approximately 135° around the periphery of said filter, and are generally equidistally separated.

8. The aspiration device according to claim 7, wherein the width of each of said openings ranges between approximately 0.125 inch and 0.3125 inch.

9. The aspiration device according to claim 2, wherein said filter element further includes a bypass block having that is secured to said filter for completely closing it; and
    wherein said bypass block includes at least one inlet port and one outlet port for allowing the liquid content of the body fluid and irrigation fluid to pass through and outside said filter element via an egress tube.

10. The aspiration device according to claim 9, further including a locking mechanism that interlocks said separating element with said housing in a releaseable engagement.

11. The aspiration device according to claim 10, wherein said locking mechanism includes a counterbore that provides a seat for a seal that provides a fluid tight seal.

12. The aspiration device according to claim 10, wherein said separating element further includes a handle that facilitates the assembly and disassembly of the aspiration device.

13. The aspiration device according to claim 11, wherein said handle includes a central bore for allowing said egress tube to pass therethrough.

14. The aspiration device according to claim 13 being fabricated from metal for optimal structural integrity and to enable it to be sterilized and reused repeatedly.

15. The aspiration device according to claim 14, wherein said metal is stainless steel.

16. The aspiration device according to claim 13 being fabricated of plastic material.

17. The aspiration device according to claim 1 for use as a surgical suction tip.

18. A method of using an aspiration device for separating liquid content of a body fluid and irrigation fluid if any, from solid matters, comprising the steps of:
    a) assembling the aspiration device by:
        holding an integrally formed housing with one hand, said housing including a proximal segment for defining a hollow space to receive part of said separating element; and inserting with the other hand an integrally formed separating element designed to be detachably inter-connectable to said housing, said separating element including:
            a filter element for separating the liquid content of the body fluid and irrigation fluid from the solid matters, said filter element having a free, open, distal end for collecting the solid matters in the interior of said filter element, as the body fluid and irrigation fluid from the interior of said filter element to an inner chamber within said hollow space and defined by said housing proximal end and the outer surface of said filter element;
            an end connector for interlocking said separating element with said housing; and
            an egress tube for conveying the separated liquid content from said inner chamber outside the aspiration device; and
        wherein said separating element being detachable from said housing in a single integral piece.
        then locking said housing and said separating element into engagement with said housing; and
    b) disassembling the aspiration device by:
        unlocking said separating for disengagement from said housing; and
        pulling said separating element away from said housing.

19. The method according to claim 18, wherein said step of assembling the aspiration device further includes the step of holding said filter coaxially within, and at a distance from said housing, to form an inner chamber between said separating element and said housing proximal segment.

20. A method of making an aspiration device for separating liquid content of a fluid from solid matters, comprising the steps of:

forming an integral housing;

forming an integral separating element detachably interconnectable to said housing;

said housing including a proximal segment for defining a hollow space to receive part of said separating element;

said separating element including:

a filter element for separating the liquid content of the fluid from the solid matters and for collecting the solid matters, said filter element having a free, open, distal end in the interior of said filter element;

an end connector for interlocking said separating element with said housing; and an egress tube for conveying the separated liquid content outside the aspiration device;

wherein said separating element being detachable from said housing in a single integral piece.

* * * * *